United States Patent [19]

Jacobs

[11] 4,196,295
[45] Apr. 1, 1980

[54] PIPERIDYL PHENYL NITRO CYCLOBUTANE DERIVATIVES

[75] Inventor: Martin J. Jacobs, Terre Haute, Ind.

[73] Assignee: International Minerals and Chemical Corporation, Libertyville, Ill.

[21] Appl. No.: 910,711

[22] Filed: May 30, 1978

[51] Int. Cl.$^2$ .......................................... C07D 295/06
[52] U.S. Cl. ..................................... 546/232; 424/267
[58] Field of Search ...................... 260/293.72, 293.83, 260/293.84; 546/232

[56] References Cited

U.S. PATENT DOCUMENTS 3,369,024  2/1968  Brannock ........................ 260/293.72

OTHER PUBLICATIONS

Kuehne et al., "J. Org. Chem.," vol. 30, pp. 4280–4283, (1965).

*Primary Examiner*—Alan L. Rotman
*Assistant Examiner*—Robert T. Bond
*Attorney, Agent, or Firm*—Bernard & Brown

[57] ABSTRACT

Compounds of the following formula and a method for their preparation are disclosed:

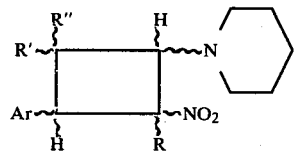

wherein Ar is substituted or unsubstituted phenyl, R, R' and R" may be similar or dissimilar and are each selected from the group consisting of lower alkyl of from 1 to about 5 carbon atoms. The compounds of this invention are useful as antimicrobial agents.

11 Claims, No Drawings

PIPEAIDYL PHENYL NITRO CYCLOBUTANE DERIVATIVES

BACKGROUND OF THE INVENTION

This invention relates to antimicrobial compounds and, more particularly, to compounds useful for the inhibition of microorganisms such as bacteria and fungi in media likely to be infected with such microorganisms.

Phenylnitrocyclobutane derivatives similar to the compounds of the present invention are known in the art. Such compounds are described, for instance, by Kuehne, M. E., et al., *J. Org. Chem.* 30, 4280–4284 (1965) and by Brannock, K. C., et al., *J. Org. Chem.* 29, 801 (1964). Such compounds are prepared by reacting an enamine with nitrostyrene, thereby yielding compounds represented by the following structural formula:

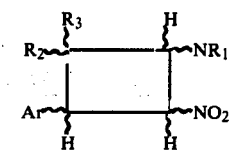

wherein Ar is phenyl and the $R_1$, $R_2$ and $R_3$ substituents depend upon the particular enamine employed in the reaction.

In the compounds disclosed in the aforementioned references, the carbon atom to which the nitro group is bonded also has a hydrogen atom bonded thereto. It has been found that such compounds possess no significant antimicrobial activity, e.g. antibacterial or antifungal activity, and, furthermore, they are not sufficiently stable to normal conditions of temperature and humidity to be useful as commercial products.

SUMMARY OF THE INVENTION

In accordance with the present invention, there is provided a compound of the formula

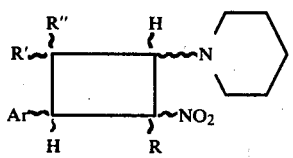

wherein Ar is substituted or unsubstituted phenyl, and R, R' and R" are similar or dissimilar and are each selected from the group consisting of lower alkyl of from 1 to about 5 carbon atoms.

DETAILED DESCRIPTION OF THE INVENTION

The compounds of the present invention are prepared by reacting an appropriate enamine with a β-alkyl-β-nitrostyrene, or a derivative thereof according to the following reaction:

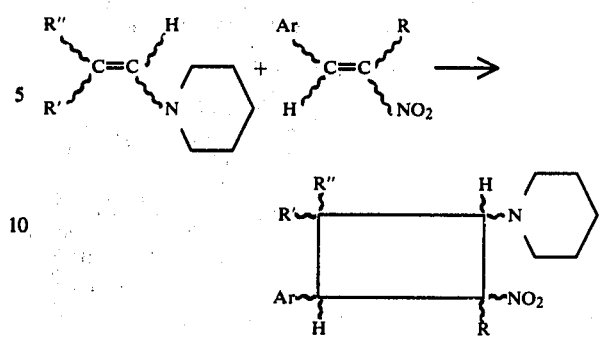

The phenyl group may be unsubstituted or may be substituted in one or more positions with such substituents as halogen, e.g. chloro, bromo, iodo, fluoro, hydroxy, lower alkoxy, e.g. having from 1 to about 5 carbon atoms, or alkyl, e.g. having from 1 to about 5 carbon atoms. R, R' and R" are lower alkyl from 1 to about 5 carbon atoms.

The reactants may be mixed together without a solvent or may be dissolved in a suitable solvent which does not react deleteriously with the reactants or the product. Suitable solvents include alcohols, such as methanol or ethanol; ethers, such as ethyl ether or tetrahydrofuran; aliphatic hydrocarbons, such as hexane or heptane; and aromatic hydrocarbons, such as benzene or toluene. The reaction is advantageously conducted at an elevated temperature, e.g. above about 40° C. and preferably from about 60° C. to about 100° C., for a time sufficient to effect a substantial production of the product. Reaction times in the range of from about 1 hour to about 15 hours, preferably from about 6 hours to about 12 hours, are generally employed.

The reaction product may be recovered and purified by conventional means. Recrystallization from hexane and methanol have been used to purify the product, and further purification may be effected by column chromatography. The compounds produced by the reaction may exist in several diastereomeric forms, and the chemical formulae depicted herein are intended to represent all of such forms. The present invention is not limited to compounds of any particular diastereomeric form but embraces all diastereomers or mixtures thereof.

The nitrocyclobutane derivatives of the present invention have been found to possess a wide spectrum of antimicrobial activity. That is, the compounds are effective for controlling or inhibiting the growth of microorganisms, including bacteria and fungi, in media infected with such organisms.

The compounds of this invention may be used to preserve or disinfect products subject to microbiological degradation. The amount of compound added to such products will depend on the nature of the product and the type and degree of microbial infection. The compounds are useful for preserving products such as pharmaceuticals, cosmetics, starch pastes, dispersion dyes, cutting and drilling oils, leather tanning solutions, paints and the like. The compounds are generally employed in such products in antimicrobially effective concentrations. Such concentrations generally range from about 0.01% to about 3% by weight of the product and preferably fall within the range of from about 0.1% to 1% by weight.

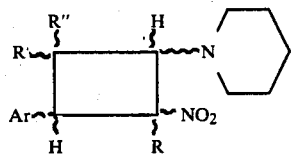

where Ar is phenyl, and R, R' and R" are similar or dissimilar and are each selected from the group consisting of lower alkyl of from 1 to about 5 carbon atoms.

3. The compound of claim 1 wherein R is methyl and R' and R" are similar or dissimilar and are each selected from the group consisting of lower alkyl of from 1 to about 5 carbon atoms.

4. The compound of claim 1 wherein R, R' and R" are each methyl.

5. A method for preparing a product compound of the formula

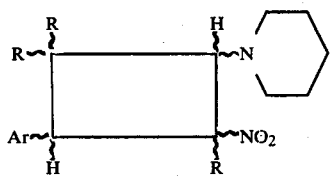

comprising reacting a compound of the formula

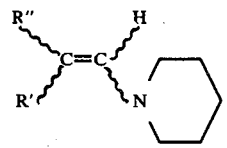

with a compound of the formula

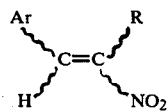

at an elevated temperature of above about 40° C. for a time sufficient to effect substantial production of said product compound; wherein Ar is phenyl, and R, R', and R" are similar or dissimilar and are each selected from the group consisting of lower alkyl of from 1 to about 5 carbon atoms.

6. The method of claim 5 wherein the temperature at which the reaction is conducted is from about 40° C. to about 100° C.

7. The method of claim 5 wherein the temperature at which the reaction is conducted is from about 60° C. to about 100° C.

8. The method of claim 6 wherein the reaction is conducted in the presence of a solvent which does not react with the reactant or the product.

9. A method for preparing a product compound of the formula:

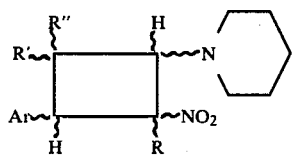

comprising reacting a compound of the formula

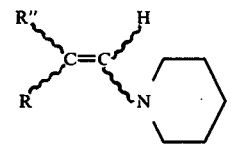

with a compound of the formula

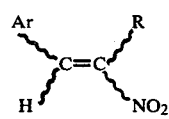

at an elevated temperature of above about 40° C. for a time sufficient to effect substantial production of said product compound; wherein Ar is phenyl substituted in one or more positions with substituents selected from the group consisting of halogen, hydroxy, lower alkoxy of from 1 to about 5 carbon atoms, and lower alkyl having from 1 to about 5 carbon atoms; and wherein R, R', and R" are similar or dissimilar and are each selected from the group consisting of lower alkyl of from 1 to about 5 carbon atoms.

10. The method of claim 8 wherein R is methyl and R' and R" are similar or dissimilar and are each selected from the group consisting of lower alkyl of from 1 to about 5 carbon atoms.

11. The method of claim 8 wherein R, R' and R" are each methyl.

* * * * *

UNITED STATES PATENT AND TRADEMARK OFFICE
CERTIFICATE OF CORRECTION

PATENT NO. : 4,196,295  
DATED : April 1, 1980  
INVENTOR(S) : Martin J. Jacobs

It is certified that error appears in the above—identified patent and that said Letters Patent is hereby corrected as shown below:

Claim 3, line 1, amend the claim to depend from "claim 1 or 2".

Claim 4, line 1, amend the claim to depend from "claim 1 or 2".

Claim 5, delete the first structural formula and replace it with the following formula:

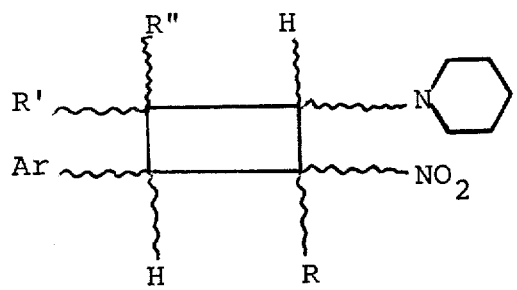

Renumber claim 9 as claim 6.

Renumber claim 6 as claim 7 and amend it to depend from "claim 5 or 6".

Renumber claim 7 as claim 8 and amend it to depend from "claim 5 or 6".

Renumber claim 8 as claim 9 and amend it to depend from "claim 7".

UNITED STATES PATENT AND TRADEMARK OFFICE
CERTIFICATE OF CORRECTION

PATENT NO. : 4,196,295
DATED : April 1, 1980
INVENTOR(S) : Martin J. Jacobs

It is certified that error appears in the above—identified patent and that said Letters Patent is hereby corrected as shown below:

Claim 10, line 1, amend the claim to depend from "claim 5 or 6".

Claim 11, line 1, amend the claim to depend from "claim 9".

Signed and Sealed this

Nineteenth Day of August 1980

[SEAL]

Attest:

*Attesting Officer*

SIDNEY A. DIAMOND

*Commissioner of Patents and Trademarks*